United States Patent
Camden

(10) Patent No.: US 6,423,734 B1
(45) Date of Patent: *Jul. 23, 2002

(54) METHOD OF PREVENTING CANCER

(75) Inventor: James Berger Camden, West Chester, OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 56 days.

This patent is subject to a terminal disclaimer.

(21) Appl. No.: 09/374,717

(22) Filed: Aug. 13, 1999

(51) Int. Cl.$^7$ .............................................. A61K 31/415
(52) U.S. Cl. ...................... 514/388; 514/387; 514/395
(58) Field of Search ................................. 514/388, 387, 514/395

(56) References Cited

U.S. PATENT DOCUMENTS

| | | | |
|---|---|---|---|
| 3,010,968 A | 11/1961 | Loux | 260/309.2 |
| 3,370,957 A | 2/1968 | Wagner et al. | 99/90 |
| 3,499,761 A | 3/1970 | Dersch | |
| 3,541,213 A | 11/1970 | Klopping | 424/273 |
| 3,669,969 A | 6/1972 | Lunn | 260/256.4 |
| 3,738,995 A | 6/1973 | Adams et al. | 260/309.2 |
| 3,881,014 A | 4/1975 | Regel et al. | 424/273 |
| 3,956,262 A | 5/1976 | Heyes et al. | 260/140 |
| 4,046,906 A | 9/1977 | Frensch et al. | 424/273 |
| 4,731,366 A | 3/1988 | Munro et al. | 514/278 |
| 4,814,329 A | 3/1989 | Harsanyi et al. | 514/396 |
| 5,098,923 A | 3/1992 | Karjalainen et al. | 514/396 |
| 5,114,951 A | 5/1992 | King | 514/290 |
| 5,149,527 A | 9/1992 | Weisenthal | |
| 5,290,801 A | 3/1994 | Higley et al. | 514/395 |
| 5,310,748 A | 5/1994 | Wilde et al. | 514/395 |
| 5,329,012 A | 7/1994 | Anderson | 548/318.5 |
| 5,364,875 A | 11/1994 | Wilde | 514/375 |
| 5,434,163 A | 7/1995 | Edlind et al. | 514/310 |
| 5,629,341 A | 5/1997 | Camden | |
| 5,656,615 A | 8/1997 | Camden | |
| 5,665,713 A | 9/1997 | Camden | |
| 5,665,751 A | 9/1997 | Camden | |
| 5,767,138 A | * 6/1998 | Camden | 514/396 |
| 5,770,616 A | 6/1998 | Camden | |
| 5,840,742 A | 11/1998 | Camden | |
| 5,854,231 A | 12/1998 | Camden | |
| 5,872,142 A | 2/1999 | Camden | |

(List continued on next page.)

FOREIGN PATENT DOCUMENTS

| | | |
|---|---|---|
| BE | 667158 | 11/1965 |
| EP | 617968 | 10/1994 |
| FR | 2155888 | 5/1973 |
| JP | 07 277 956 | 10/1995 |
| WO | WO 94/04541 | 3/1994 |
| WO | WO 96/32103 | 10/1996 |
| WO | WO 96/32104 | 10/1996 |
| WO | WO 96/32107 | 10/1996 |
| WO | WO 96/32115 | 10/1996 |
| WO | WO 96/40119 | 12/1996 |
| WO | WO 96/40120 | 12/1996 |
| WO | WO 96/40122 | 12/1996 |

(List continued on next page.)

OTHER PUBLICATIONS

Vergieva, Khig. Zdraveopaz., 25(4), 333–9 Abstract Only, 1982.*
Roget's Inernational Thesaurus, Third Ed. ,pp 453 and 1066, 1962.*
Brown, et al., J. Am. Chem. Soc., 83:1764–65 (1961).
Grenda, et al., J. Org. Chem. 30,259 (1965).
W. T. Thomson, Agricultural Chemicals Book IV, Fungicides, pp. 154, 121, 123, 1993–1994 Revision no date.
Carter, W.A. CRC Press, Selective Inhibitors of Viral Functions, pp. 277–346 (1975).
Merck Index, Eighth Edition, 1968, p. 1035.
DuPont, Material Safety Data Sheet Benlate Fungicide, Sep. 27, 1994.
Derwent Publications, AN 95–400884 and Japan Patent Abstracts, JP 07 277956, Oct. 1995.
Teicher, et al., Breast Cancer Research and Treatment, vol. 36, No. 2, pp 227–236 (1995).

(List continued on next page.)

Primary Examiner—Jerome D. Goldberg
(74) Attorney, Agent, or Firm—Bart S. Hersko

(57) ABSTRACT

Methods of treating and inhibiting cancerin animals by administering a therapeutically effective amount of a pharmaceutical composition having benzimidazole of the general formula:

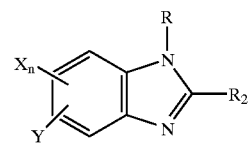

wherein X is hydrogen, halogen, alkyl of less than 7 carbon atoms or alkoxy of less than 7 carbon atoms; n is a positive integer of less than 4; Y is hydrogen, chlorine, oxychloro, nitro, methyl or ethyl; and R is hydrogen, or an alkyl group of from 1 to 8 carbon atoms and $R_2$ is $NHCOOR_1$ wherein $R_1$ is aliphatic hydrocarbon of less than 7 carbon atoms, and preferably an alkyl group of less than 7 carbon atoms and pharmaceutically acceptable derivatives alone, or in combination, or in conduction with other therapeutic agents such as other cancer inhibiting compounds, and operative combinations thereof.

28 Claims, No Drawings

U.S. PATENT DOCUMENTS

| | | |
|---|---|---|
| 5,880,144 A | 3/1999 | Camden |
| 5,900,429 A | 5/1999 | Camden |
| 5,902,804 A | 5/1999 | Camden |
| 5,908,855 A | 6/1999 | Camden |
| 5,929,099 A | 7/1999 | Camden |
| 5,932,604 A | 8/1999 | Camden |
| 5,932,609 A | 8/1999 | Camden |
| 6,025,377 A | 2/2000 | Camden |
| 6,077,862 A | 6/2000 | Camden |

FOREIGN PATENT DOCUMENTS

| | | |
|---|---|---|
| WO | WO 97/05870 | 2/1997 |
| WO | WO 97/05872 | 2/1997 |
| WO | WO 97/05873 | 2/1997 |
| WO | WO 98/32440 | 2/1998 |
| WO | WO 98/51303 | 11/1998 |
| WO | WO 98/51304 | 11/1998 |
| WO | WO 99/59585 | 11/1999 |

OTHER PUBLICATIONS

Bissery, et al., Seminars in Oncology: Management of Breast Cancer: A New Therapeutic Approach, vol. 22, No. 6–S13, pp. 3–16, (1995).
Pending Application of Camden, Serial No. 09/264,942, filed Mar. 9, 1999. (5638D2C).
Pending Application of Camden, Serial No. 09/375,173, filed Aug. 16, 1999. (5702CR).
Pending Application of Camden, Serial No. 09/469,389, filed Dec. 22, 1999. (5703D2C).
Pending Application of Camden, Serial No. 09/360,499, filed Jul. 26, 1999. (5781D).
Pending Application of Camden, Serial No. 08/674,182, filed Jul. 16, 1996, CPA filed Feb. 10, 1999. (5782).
Pending Application of Camden, Serial No. 09/245,520, filed Feb. 5, 1999. (5782D).
Pending Application of Camden, Serial No. 09/220,914, filed Dec. 24, 1998. (5783C).
Pending Application of Camden, Serial No. 09/371,457, filed Aug. 10, 1999. (5784R).
Pending Application of Camden, Serial No. 09/371,459, filed Aug. 10, 1999. (5784R2).
Pending Application of Camden, Serial No. 09/364,021, filed Jul. 30, 1999. (5785D2).
Pending Application of Camden, Serial No. 09/408,664, filed Sep. 29, 1999. (5785D2R).
Pending Application of Camden, Serial No. 09/312,948, filed May 17, 1999. (5786D).
Pending Application of Camden, Serial No. 09/394,383, filed Sep. 10, 1999. (5786DR).
Pending Application of Camden, Serial No. 09/394,382, filed Sep. 10, 1999. (5786DR2).
Pending Application of Camden, Serial No. 09/218,884, filed Dec. 22, 1998. (6496D).
Pending Application of Camden, Serial No. 08/857,811, filed May 16, 1997, CPA filed Jul. 28, 1999. (6643).
Pending Application of Camden, Serial No. 09/312,949, filed May 17, 1999. (7161R).
Pending Application of Camden, Serial No. 09/374,717, filed Aug. 13, 1999. (7719).
Pending Application of Camden, Serial No. 09/552,408, filed Apr. 19, 2000. (6496D2).
Pending Application of Camden, Serial No. 09/552,825, filed Apr. 20, 2000. (6643D2).
Pending Application of Camden, Serial No. 09/552,820, filed Apr. 20, 2000. (6643D3).
Pending Application of Camden, Serial No. 09/560,059, filed Apr. 27, 2000. (5781D3).
Pending Application of Camden, Serial No. 09/603,040, filed Jun. 26, 2000. (5781DC).
Pending Application of Camden, Serial No. Not Yet Correctly Assigned, Assigned same SN as 8069, filed Apr. 28, 2000. (8068).
Pending Application of Camden, Serial No. Not Yet Correctly Assigned, Assigned same SN as 8068, filed Apr. 28, 2000. (8069).
Pending Application of Camden, Serial No. 09/602,170, filed Jun. 22, 2000. (5783C2).
Pending Application of Camden, Serial No. 09/603,322, filed Jun. 26, 2000. (5781D2).
Chemical Abstracts 65:6570h referring to BE patent, date Nov. 16, 1965.
Lapras, M. et al. Bull. Soc. Sci. Vet. et Med. comparee, Lyon, 1975, vol. 77, No. 6, pp. 379–397 (in French)—and English translation thereof.
Delatour et al., Therapie, vol. 31, No. 4., pp. 505–515, (1976), and translation thereof.
Elgebaly et al. , J. Natl. Cancer Inst., vol. 74, No. 4, pp. 811–815 (1985).
Friedman, et al., Biochimica et Biophysica Acta, 544 (1978) pp. 605–614.
Lacey, et al., Biochemical Pharma, vol. 34, No. 19, pp. 3603–3605 (1985).
Chemical Abstracts 121:175012z, (1994) p 607, Katiyar, et. al.
Stedman's Medical Dictionary, $24^{th}$ ed., 1983, pp. 777–778.
Aur, J. Pediatr., 78, No. 1, (1971) pp. 129–131.
Lundy et al., Cancer Treat. Rep., vol. 62, No. 11, (1978), pp. 1955–1962.
Lundy et al., Surg. Forum, vol. 27, No. 62 (1976) pp. 132–134.
Marinovich, et al., Toxicol., vol. 94, No. 1–3, (1994) pp 173–85.
Lovett, Diss. Abstr. Int., (Sci), vol. 39, No. 11, (1979) pp. 5315–5316.
Brabender, et al., Cancer Research, vol. 36 (Mar., 1976) pp. 905–916.
Atassi et al., Europ., J. Cancer, vol. 11 (1975) pp. 599–607.
Chemical Abstracts 113:112365 (1990) Ghannoum, et al.
Ram, et al., J. Med. Chem., 35, No. 3, 539–547 (1992).
Nene, et al., International Science Publisher, Fungicides in Plant Disease Control, Chapter 9, 1993.
Private Communication to Dr. Von Hoff from National Institute of Health, National Cancer Society (1995).
Chemical Abstracts 92:123231 (1979) Menzel et al.
Lacey et al., International Journal for Parasitology, vol. 18 No. 7, pp 885–936 (1988).
Merck Index, $12^{th}$ ed., 7943 and 9877, Merck & Co. (NJ 1996).
Chemical Abstracts 102:217569 (1985) Elgebaly et al.
Chemical Abstracts 87:161659 (1997) Lundy et al.
Lacey, et al., Biochemical Pharma., vol. 34, No. 7, pp. 1073–1077 (1985).
Lassnau, et al., Chest, vol. 104, pp 119–122 (1993).
Georgopapadakov et al., Science vol. 264, pp. 371–373 (Apr. 15, 1994).
Carter et al., Chemotherapy of Cancer, $2^{nd}$ Ed., John Wiley & Sons, NY, NY (1981), pp. 362–365.
Chemical Abstracts 98:66765, Vergieva (1983).

* cited by examiner

METHOD OF PREVENTING CANCER

TECHNICAL FIELD

The present invention relates to methods of using one or more benzimidazole compounds and its pharmaceutically acceptable derivatives to treat and prevent cancer in both both human and warm blooded animals. In particular, this invention relates to benzimidazole and its derivatives in cancer prevention and maintenance therapy.

BACKGROUND OF THE INVENTION

Cancers are a leading cause of death in animals and humans. The exact cause of cancer is not known. There is evidence that certain activities such as smoking or exposure to carcinogens may enhance the risk for certain types of cancers and tumors.

Treatment of cancer in the early stages typically comprise local treatment such as, surgery and/or radiotherapy. While radiation therapy has been widely used in managing cancerous diseases, it is limited by lack or radiosensitivity of specific regions of malignant tumors. More advanced disease is treated by combining local treatment with chemotherapy. Although current chemotherapeutic agents have been shown to be effective against cancers and tumor cells, the use of combined treatment with all three regimens, surgery, radiotherapy, and chemotherapy, have not been shown to be effective against all cancer and tumor cells.

Much of the effort in therapeutics of cancer has focused on cancers that are metastasized. To date hormones, in particular estrogen, progesterone and testosterone, and some antibiotics produced by a variety of microbes, alkylating agents, and anti-metabolites form the bulk of therapies available to oncologists. Prostate cancer treatments, for example, rely on hormonal manipulation. However, in despite the initial high response rate, patients often develop hormone-refractory tumors. Unfortunately, the clinical usefulness of these treatments have been limited. This is because these therapies demonstrate only marginal levels of activity or generally unacceptable levels of cytotoxicity or both, thereby diminishing their usefulness in cancer treatment. Overall the results of cytotoxic chemotherapy have been disappointing indicating a long felt need for a new approach or treatment. Ideally cytotoxic agents that have specificity for cancer and tumor cells while not affecting normal cells would be extremely desirable. Unfortunately, none have been found and instead agents which target especially rapidly dividing cells (both tumor and normal) have been used.

SUMMARY OF THE INVENTION

A method of preventing cancer in a patient, especially colon cancer is disclosed. The patients are treated utilizing a benzimidazole compounds. its pharmaceutical addition salts, pharmaceutically acceptable derivatives or its prodrugs selected from the group having the formula:

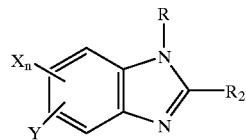

wherein X is hydrogen, halogen, alkyl of less than 7 carbon atoms or alkoxy of less than 7 carbon atoms; n is a positive integer of less than 4; Y is hydrogen, chloro, oxychloro, nitro, methyl or ethyl; and R is hydrogen, or an alkyl group of from 1 to 8 carbon atoms and $R_2$ is $NHCOOR_1$ wherein $R_1$ is aliphatic hydrocarbon of less than 7 carbon atoms, and preferably an alkyl group of less than 7 carbon atoms is claimed.

Preferably the subjects are treated with compounds having the formula:

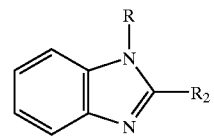

wherein R is an alkyl of 1 through 8 carbon atoms and $R_2$ is selected from the group consisting of $NHCOOR_1$, wherein $R_1$ is methyl, ethyl or isopropyl and the non-toxic, pharmaceutically acceptable acid addition salts with both organic and inorganic acids. The most preferred compound is 2-methoxycarbonylamino-benzimidazole and its pharmaceutically acceptable salts.

Specifically, the invention provides a method of preventing various cancers associated with neoplasm or malignant tumors, for example, leukemia, sarcomas and lymphomas including prostate cancer, breast cancer, lung cancer, melanoma, and the like.

The present invention provides a method of treatment in a subject comprising administering a therapeutic amount of benzimidazole or a pharmaceutically acceptable derivative to humans or animals.

DETAILED DESCRIPTION OF THE INVENTION

A. DEFINITIONS

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "therapeutically effective amount" is meant an amount of a compound of the present invention effective to yield a desired therapeutic response. For example to prevent cancer or treat the symptoms of cancer in a host or an amount effective to treat cancer. The specific "therapeutically effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" is salt of the benzimidazole compound with an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-cancer agent to the animal or human. The carrier may be liquid or solid and is selected with the planned manner of administration in mind.

As used herein, "cancer" refers to all types of cancers or neoplasm or malignant tumors found in mammals. Cancer includes sarcomas, lymphomas and other cancers. The following types are examples, but are, but is not intended to be limited to these particular types of cancers: prostate, colon, breast, both the MX-1 and the MCF lines, pancreatic, neuroblastoma, rhabdomysarcoma, lung, murine, melanoma, leukemia, pancreatic, melanoma, ovarian, brain, head & neck, kidney, mesothelioma, sarcoma, Kaposi's, sarcoma, stomach, and uterine.

As used herein, the term "cell" include but is not limited to mammalian cells (e.g., mouse cells rat cells or human cells).

As used herein, the "anti-cancer compounds" are the benzimidazoles, their salts, and prodrugs thereof. The exact benzimidazoles are described in detail below. The preferred materials are the products sold under the names "benomyl®" or "carbendazim®" by BASF and Hoechst, DuPont and MSD-AgVet.

As used herein, the term "inventive group" refers to the benzimidazoles, and their salts or prodrugs.

As used herein, "a subject in need thereof" is a patient, animal, mammal or human, who will benefit from the method of this invention. This patient may be a person genetically disposed to cancer or a patient who is believed to be at risk for developing cancer.

As used herein, the term "prodrugs" are considered to be any covalently bonded carriers which release the active parent drug according to the formula of derivatives described above in vivo, in vitro or ex vivo. Prodrugs of the benzimidozole or urea derivatives are prepared by modifying functional groups present in the compounds in such a way that the modifications are cleaved, either in routine manipulation or in vivo, in vitro, or ex vivo to the parent compounds. Prodrugs include compounds wherein free hydroxyl, sulfhydryl, or amine groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the arylthiazolyl thiourea derivatives or arylthiazoloyl urea derivative; phosphate esters, dimethylglycine esters, aminoalkylbenzyl esters, aminoalkyl esters and carboxyalkyl esters of alcohol and phenol functional groups in the arylthiazolyl thiourea derivatives or arylthiazoloyl urea derivative; and the like.

B. METHOD OF THE PRESENT INVENTION

The present invention provides a method for reducing or inhibiting infected cells or population of cells by administering an effective amount of a benzimidazole compound and/or pharmaceutically acceptable derivatives, such that (1) cancer is prevented and (2) metastasis and spreading of cancerous is inhibited, and (3) the life of the patient is prolonged.

The compounds used in the method of the present invention are known for their antifungal activities. They are systemic fungicides used to prevent and eradicate fungi. In the method of the present invention the compounds have been found to have anticancer activity. The compounds used alone and/or when combined with carriers, provide compositions for treating and preventing the spreading of cancer in vitro, ex vivo or in vivo. The compounds can be combined with various pharmaceutically acceptable carriers as defined below.

C. METHOD OF ADMINISTERING THE ANTI-CANCER COMPOUND AND DOSAGE DELIVERY FORMS

The compounds of the present invention can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into or around the tumor.

The dosage amounts are based on the effective inhibitory concentrations observed in antitumorigencity studies. The preferred route will vary with the (1) condition and age of the recipient, (2) tumor being treated (3) nature of tumor and (4) desired blood levels. It is believed that parenteral treatment by intravenous, subcutaneous, or intramuscular application of the compounds of the present invention formulated with an appropriate carrier, other anticancer agents or compounds or diluents to facilitate application will be the preferred method of administering the compounds to warm blooded animals.

The benzimidazole compounds, pharmaceutically acceptably derivatives, in particular 2-methoxycarbonylamino-benzimidazole and its pharmaceutically acceptable salts or prodrugs are preferably micronized or powdered so that it is more easily dispersed and solubilized by the body. Processes for grinding or pulverizing drugs are well known in the art. For example, a hammer mill or similar milling device can be used. The preferred particle size is less than about $100\mu$ and preferably less than $50\mu$. These compounds are not very soluble, and therefore are preferably given in tablet form or as a suspension. Suitable methods of administering the compounds of the present invention and dosage forms can be found herein below.

The benzimidazole compounds or pharmaceutically acceptable derivatives of this invention can be administered as treatment for cancer by any means that produces contact of the active agent with the agent's site of action in the body. They can be administered by any conventional means available for use in conjunction with pharmaceuticals, either as individual therapeutic agents or in a combination of therapeutic agents. Preferably the compounds of the present invention are administered as a pharmaceutical formulation comprising at least one compound of the present invention, as defined above, together with one or more pharmaceutically acceptable carriers. It can be co-administered in the form of a tablet or capsule, as an agglomerated powder or in a liquid form or as a lipsome.

The compounds of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

The benzimidazole compounds or therapeutically acceptable derivatives of the present invention can also be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

1. Combination Therapy

The compounds of the present invention may additionally be combined with other anticancer compounds to provide an operative combination. It is intended to include any chemically compatible combination of a compound of this inventive group with other compounds of the inventive group or other compounds outside of the inventive group, as long as the combination does not eliminate the anticancer activity of the compound of this inventive group. For example, one or more benzimidazole compounds or therapeutically acceptable derivatives can be combined with other anticancer agents, chemotherapeutic agents, or potentiators. Potentiators are materials which affect the body's response to the anti-cancer agent.

The combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disease being treated, the severity of the infection and the response to the treatment. As used herein, "adjunct therapy" means that the patient in need of the drug is treated or given another drug for the disease and/or a potentiator in conjunction with the compound of the inventive gorup. Adjunct therapy can be sequential therapy where the patient is treated first with one compound and then the other within a given time period or concommitant therapy where the two compounds are administered substantially simultaneously or in overlapping dosing regimens.

The benzimidazole compound generally is used in single or multiple treatments. Alternatively, the benzimidazole compound is combined with other therapeutic agents, chemotherapeutic agents or potentiators to treat disorders. "Potentiators" are materials which affect the body's response or diseased cell's response to the benzimidazole compound. A "potentiator" can be any material which improves or increases the efficacy of a pharmaceutical composition containing the benzimidazole compound or acts as an immunomodulator to increase the efficacy of the benzimidazole compound.

An exemplary potentiator is triprolidine or its cis-isomer which are used in combination with chemotherapeutic agents and a benzimidazole compound. Triprolidine is described in U.S. Pat. No. 5,114,951 (1992). Another potentiator is procodazole, 1H-Benzimidazole-2-propanoic acid; [β-(2-benzimidazole) propionic acid; 2-(2-carboxyethyl) benzimidazole; propazol]. Procodazole is a non-specific immunoprotective agent active against viral and bacterial infections that is used with the compositions claimed herein. It is effective with a benzimidazole compound in the methods of the invention. Procodazole can also be combined with a benzimidazole compound and other chemotherapeutic agents and used in the method of the invention. Other potentiators which can be used with a benzimidazole compound, and optionally another chemotherapeutic agent, in the methods of the invention include macrophage colony-stimulating factor (M-CSF), 7-thia-8-oxoguanosine, 6-mercaptopurine and vitamin A (retinol), monensin, an anti-sense inhibitor of the RAD51 gene, bromodeoxyuridine, dipyridamole, indomethacin, a monoclonal antibody, an anti-transferrin receptor immunotoxin, metoclopramide, N-solanesyl-N,N'-bis(3,4-dimethoxybenzyl)ethylenediamine, leucovorin, heparin, N-[4-[(4-fluorphenyl)sulfonly]phenyl]acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide.

The chemotherapeutic agents which can be used with a benzimidazole compound and an optional potentiator are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. For a detailed discussion of chemotherapeutic agents and their method of administration, see Dorr, et al, *Cancer Chemotherapy Handbook*, 2d edition, pages 15–34, Appleton & Lange (Connecticut, 1994) the disclosure of which is hereby incorporated by reference.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposde; and the DNA minor groove binder Plcamydin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

Aziridine such as Thiotepa;

methanesulphonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine.

DNA strand breaking agents include Bleomycin.

DNA topoisomerase II inhibitors include the following:

Intercalators, such as Amsacrine, Dactinomycin, Daunorubicin, Doxorubicin, Idarubicin, and Mitoxantrone; and nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacitidine and Floxuridine purine antagonists such as Mercaptopurine, 6-Thioguanine, Pentostatin;

sugar modified analogs such as Cytarabine and Fludarabine; and ribonucleotide reductase inhibitors such as hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include coichicine, Vincristine and Vinblastine, both alkaloids and Paclitaxel and cytoxan.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlortrianisen and Idenestrol;

progestins such as Hydroxyprogesterone caproate, Medroxyprogesterone, and Megestrol; and androgens such as testosterone, testosterone propionate; fluoxymesterone, methyltestosterone.

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamoxifen, antiandrogen agents such as Flutamide; and antiadrenal agents such as Mitotane and Aminoglutethimide.

Hydroxyurea, which appears to act primarily through inhibition of the enzyme ribonucleotide reductase, can also be used in combination with the benzimidazole compound.

Asparaginase is an enzyme which converts asparagine to nonfunctional aspartic acid and thus blocks protein synthesis in the tumor. Asparaginase can also be used in combination with the benzimidazole compound to treat cancer.

Other chemotherapeutic benzimidazoles and griseofulvin can also be used in combination with the benzimidazole compound and optionally a potentiator to treat or inhibit the growth of cancer or extend the life span of a mammal having cancer.

The amount and identity of a chemotherapeutic agent that is used with a benzimidazole compound in the methods of the invention will vary according to cellular response, patient response and physiology, type and severity of side effects, the disease being treated, the preferred dosing regimen, patient prognosis or other such factors.

The benzimidazole compound can be used in combination with one or more other agents or combination of agents known to possess anti-leukemia activity including, by way of example, a-interferon; interleukin-2; cytarabine and mitoxantrone; cytarabine and daunorubicin and 6-thioguanine; cyclophosphamide and 2-chloro-2'-deoxyadenosine; VP-16 and cytarabine and idorubicin or mitoxantrone; fludarabine and cytarabine and g-CSF; chlorambucil; cyclophosphamide and vincristine and (prednisolone or prednisone) and optionally doxorubicin; tyrosine kinase inhibitor; an antibody; glutamine; clofibric acid; all-trans retinoic acid; ginseng diyne analog; KRN8602 (anthracycline drug); temozolomide and poly(ADP-ribose) polymerase inhibitors; lysofylline; cytosine arabinoside; chlythorax and elemental enteral diet enriched with medium-chain triglycerides; amifostine; gilvusmycin; or a hot water extract of the bark of, Acer nikoense.

The benzimidazole compound can also be used in combination with other non-chemotherapeutic treatments for leukemia including bone marrow transplant, therapeutic apheresis, radiation.

When a benzimidazole compound is used in combination with other therapeutic agents, the ratio of the compound of the invenition to the other therapeutic agent will be varied as needed according to the desired therapeutic effect, the observed side-effects of the combination, or other such considerations known to those of ordinary skill in the medical arts. Generally, the ratio of the benzimidazole compound to other therapeutic agent will range from about 0.5% to about 99.5% wt. to about 99.5% to about 0.5% wt.

When the benzimidazole compound is administered before or after other therapeutic agents to treat viral infections, cancer, tumors, or other diseases, the respective doses and the dosing regimen of the benzimidazole compound and the other therapeutic agent may vary. The adjunct therapy can be sequential, that is the treatment with one agent first and then the second agent, or it can be concomitant treatment wherein two or more agents are administered substantially at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disease being treated, the severity of the infection and the response to the treatment.

For example, a full dosing regimen of the benzimidazole compound can be administered either before or after a full dosing regimen of the other therapeutic agent, or alternating doses of the benzimidazole compound and the other therapeutic agent may be administered. As a further example, the benzimidazole compound can be administered concomitantly with the other therapeutic agent.

Propionic acid and its salts and esters can also be used in combination with the pharmaceutical compositions claimed herein. Antioxidant vitamins such as vitamins A, C and E and beta-carotene can be added to these compositions.

2. Unit dosage

The compounds of the present invention may administered in a unit dosage form and may be prepared by any methods well known in the art. Such methods include combining the compounds of the present invention with a carrier or diluent which constitutes one or more accessory ingredients. Typically, the formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Dosage forms (compositions suitable for administration) comprise from about 10 milligrams to about 10,000 milligrams of active ingredient per kilogram (kg) of body weight. Preferably the dosage forms will contain from about 150 mg to about 5000 mg/kg of body weight. Most preferably the doses are between 1500 mg to about 5000 mg/kg of body weight. In these pharmaceutical compositions the active ingredient will ordinarily be present in an amount of about 0.5 to about 95% by weight based on the total weight of the dosage unit.

3. Pharmaceutical Kits

The present invention also includes pharmaceutical kits useful, for example, for the treatment of cancer, which comprise one or more containers containing a pharmaceutical composition comprising a therapeutically effective amount of a benzimidazole compound or therapeutically acceptable derivative. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit. In the present disclosure it should be understood that the specified materials and conditions are important in practicing the invention but that unspecified materials and conditions are not excluded so long as they do not prevent the benefits of the invention from being realized.

4. Dosage Forms

Specific examples of pharmaceutical acceptable carriers and excipients that may be used to formulate oral dosage forms of the present invention are described in U.S. Pat. No. 3,903,297 to Robert, issued Sep. 2, 1975.

Techniques and compositions for making dosage forms useful in the present invention are described herein below.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary or paste.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin and cyclodextrin derivatives and the like.

Capsule or tablets can be easily formulated and can be made easy to swallow or chew. Tablets may contain suitable binders, lubricants, diluents, disintegrating agents, coloring agents, flavoring agents, flow-inducing agents, and melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethlcellose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or betalactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Molded tables may be made by molding in a suitable machine a mixture of the powdered active ingredient moistened with an inert liquid diluent.

The tablets may optionally be coated or scored and may be formulated so as to provide slow or controlled release of the active ingredient. Tablets may also optionally be provided with an enteric coating to provide release in parts of the gut other than the stomach.

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound which enhances absorption or penetration of the active ingredient through the skin or other affected areas. Examples of such dermal penetration enhancers include dimethylsulfoxide and related analogues.

The oil phase of the emulsions of the composition used to treat subjects in the present invention may be constituted from known ingredients in a known manner. This phase may comprise one or more emulsifiers. For example, the oily phase comprises at least one emulsifier with a fat or an oil or with both a fat and an oil or a hydrophilic emulsifier is included together with a lipophilic emulsifier which acts as a stabilizer. Together, the emulsifier(s) with or without stabilizer(s) make up an emulsifying was, and the wax together with the oil and/or fat make up the emulsifying ointment base which forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, parrafm, straight or branched chain, mono-or dibasic alkyl esters, mineral oil. The choice of suitable oils or fats for the formulation is based on achieving the desired cosmetic properties, the properties required and compatibility with the active ingredient.

The compounds may also be administered vaginally for example, as pessaries, tampons, creams, gels, pastes, foams or spray formulations containing in addition to the active ingredient. Such carriers are known in the art.

Formulations for rectal administration may be presented as a suppository with a suitable base comprising, for example, cocoa butter or a salicylate.

Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous isotonic with the blood of the intended recipient; and aqueous and non-aqueous sterile suspensions which may include suspending systems which are designed to target the compound to blood components or one or more organs. The formulations may be presented in unit-dose or multi-dose sealed containers, for example, ampoules and vials. Extemporaneous injections solutions and suspensions may be prepared from sterile powders, granules and tablets of the kind previously described.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Intravenously, the most preferred doses can range from about 1 to about 1000 mg/kg/minute during a constant rate infusion. The benzimidazole compounds or therapeutically acceptable derivatives can be administered in a single daily dose, or the total daily dosage can be administered in divided doses of two, three, or four times daily. The benzimidazole compounds or therapeutically acceptable derivatives can be given in one or more doses on a daily basis or from one to three times a week.

The present invention additionally include administering compounds of the herein described formula for the use in the form of veterinary formulations, which may be prepared, for example, by methods that are conventional in the art.

Useful pharmaceutical dosage forms for administration of the compounds of this invention are illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

Techniques and compositions for making dosage forms useful in the present invention are described in the following references: 7 Modern Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

One or more benizmidazoles can be used in a single treatment. The benzimidazoles can be combined with other chemotherapeutic agents or potentiators.

D. THE BENZIMIDAZOLE COMPOUNDS

The invention compounds are benzimidazole derivatives, their salts, pharmaceutically acceptable derivatives or their prodrugs having the following structure:

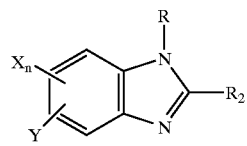

wherein X is hydrogen, halogen, alkyl of less than 7 carbon atoms or alkoxy of less than 7 carbon atoms; n is a positive integer of less than 4; Y is hydrogen, chloro, oxychloro, nitro, methyl or ethyl; and R is hydrogen or an alkyl group having from 1 to 8 carbons, and $R_2$ is $NHCOOR_1$ wherein $R_1$ is aliphatic hydrocarbon of less than 7 carbon atoms, and preferably and alkyl group of less than 7 carbon atoms.

Preferably the compounds used in the method of the present invention are:

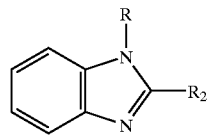

wherein R is an alkyl of 1 through 8 carbon atoms and $R_2$ is selected from the group consisting of $NHCOOR_1$, wherein $R_1$ is methyl, ethyl or isopropyl and the non-toxic, pharmaceutically acceptable acid addition salts with both organic and inorganic acids.

The most preferred compounds are 2-methoxycarbonylamino-benzimidazole and the compounds wherein Y and X are hydrogen. Also preferred are those with a chioro or oxychioro substituent in the 5 or 7 position.

These compounds are prepared according to the method described in U.S. Pat. No. 3,738,995 issued to Adams et al, Jun. 12, 1973. The thiazolyl derivatives are prepared according to the method described in Brown et al. (J. Am. Chem. Soc. (1961), 83, 1764), and Grenda et al. (J. Org. Chem. (1965), 30, 259). Some of these compounds are also commercially available from BASF, Hoechst, E. I. Du Pont de Nemours, and MSD-AgVet. A synthetic organic chemist could readily ascertain how to prepare the compounds used in this invention.

E. DOSAGE

Any suitable dosage may be given in the method of the invention. The type of compound and the carrier and the amount will vary widely depending on the species of the warm blooded animal or human, body weight, and tumor being treated. A dosage of as little as about 10 milligrams (mg) of the active ingredient may be used in the method of the present invention. Generally a dosage of about 250 milligrams (mg) per kilogram (kg) of body weight and up to about 6000 mg per kg of body weight is suitable. Preferably from 1000 mg to about 5000 mg/kg of body weight is used. Most preferably the doses are between 1500 mg to about 5000 mg. Tedoses which have shown dose responsive in vivo against cancers are 2500 mg/kg, 3500 mg/kg, 4000 mg/kg and 5000 mg/kg. These dosages are in mice and generally human dosages are about one-half (½) of the mouse dose.

Typically, the dosage in man is lower than for small warm blooded mammals such as mice. A dosage unit may comprise a single compound or mixtures thereof with other compounds or other or cancer inhibiting compounds. The dosage unit can also comprise ingredients described herein above. The unit may be in various forms and administered as described above. The unit dosage may also be used in combination with other local treatment modalities, such at surgery and/or radiotherapy.

The benzimidazole can be given in one or more doses on a daily basis or from one to three times a week.

The following examples are illustrative and are not meant to be limiting to the invention.

F. TEST METHODS

The Institute for Drug Development's In Vivo Laboratory has evaluated the chemopreventive activity of Carbendazim against the Apc$^{Min}$ mouse model and the MiaPaCa human pancreatic tumor xenograft model. In both studies,— Carbendazim was administered orally at 1000 mg/kg, 1500 mg/kg, and 2000 mg/kg on a twice weekly to end schedule. In order to provide a positive control for the Apc$^{Min}$ mouse study, Sulindac was administered ad libitum in the drinking water at 85 mg/l. Gemcitabine at 80 mg/kg, i.p., served as the positive control in the MiaPaCa study.

Apc$^{Min}$ Mouse Model

Female C57BL/6J-Apc$^{Min}$ mice were obtained from The Jackson Laboratory at 4–5 weeks of age. The following day (Day 1), drug treatment begins. The Min (Multiple intestinal neoplasia) mouse is a strain with a mutated murine Apc (*adenomatous polyposis coli*) gene, which leads to the development of multiple intestinal polyps. This development is time and diet dependent, with 100% of the mice which ingest a high fat diet forming adenomas beginning around 45 days of age. These mice develop in excess of 30 adenomas throughout the intestinal tract during their 120 day life span and are therefore an ideal model for the evaluation of potential chemopreventive agents.

The mean survival times of all groups were calculated, and results are expressed as mean survival of treated mice/ mean survival of control mice (T/C)×100%. A T/C value of 150 means that the mice in the treated group lived 50% longer than those of the control group; this is sometimes referred to as the increase in life span, or ILS value.

Statistics were performned on the data using primarily the log rank p-value test. The results are shown below in Table 1.

TABLE 1

Carbendazim vs. Min Mouse Model
Avg. Age - 118 Days

| Group | n | Dose | Route | Schedule | Tumor # ±S.D. | p-value | # of non-specific Death |
|---|---|---|---|---|---|---|---|
| Control | (10) | Peanut Oil | p.o. | 2× weekly to end | 31.70 ± 18.49 | — | 0 |
| Carbendazim | (10) | 1000 mg/kg | p.o. | 2× weekly to end | 24.71 ± 7.8 | p = 0.364 | 3 |
| Carbendazim | (10) | 1500 mg/kg | p.o. | 2× weekly to end | 13.25 ± 4.83 | p = 0.015 | 2 |
| Carbendazim | (9) | 2000 mg/kg | p.o. | 2× weekly to end | 19.17 ± 7.36 | p = 0.139 | 3 |
| Sulindac | (9) | 0.85 mg/kg | p.o. | ad libitum/H20 | 16.33 ± 4.69 | p = 0.027 | 0 |

The results with Carbendazim and the Min mouse model are shown in Table 1. The average number of intestinal tumors were 31.7 in peanut oil controls compared to 24.7, 13.2, and 19.1 in animals administered Carbendazim at 1000, 1500, and 2000 mg/kg, respectively. Animals treated with Sulindac had a mean intestinal tumor number of 16.3. Treatment with Carbendazim (1500 mg/kg) and Sulindac resulted in a significant (p<0.05) decrease in the number of intestinal tumors compared to animals given peanut oil. There was no significant difference in the number of intestinal tumors between groups administered Carbendazim at 1500 mg/kg and those treated with Sulindac. These animals had relatively few tumors at 111 days which is their normal life span Colon, Breast and Lund Tumor Cells Test The following cell culture tests were performed to test the toxicity of the benzimidazole compounds on colon, breast and lung human tumor cells. The viability of the cells were tested by looking at MTT (3-[4,5-dimethylthiazol-2-yl]-2, 5-diphenyltetrazolium bromide) reduction. MTT assay is a well known measure of cell viability.

The colon tumor cells (HT29 from American Type Culture Collection (ATCC)) and the breast cells (MX1 from cell lines from ATCC) were cultured in Eagle's Miminal Essential Medium with 10% fetal bovine serum. The lung tumor cells (A549 from ATCC cell lines) were cultured in Ham's F12 medium with 10% fetal bovine serum.

The tumor cells were passaged and seeded into culture flasks at the desired cell densities. The culture medium was decanted and the cell sheets were washed twice with phosphate buffered saline (PBS). The cells were trypsinized and triturated prior to seeding the flasks. Unless otherwise indicated the cultures were incubated at 37±1° C. in a humidified atmosphere of 5±1% carbon dioxide in air. The cultures were incubated until they were 50–80% confluent.

The cells were subcultured when the flasks were subconfluent. The medium was aspirated from the flasks and the cell sheets rinsed twice with PBS. Next, the Trypsin Solution was added to each flask to cover the cell sheet. The Trypsin Solution was removed after 30–60 seconds and the flasks were incubated at room temperature for two to six minutes. When 90% of the cells became dislodged, growth medium was added. The cells were removed by trituration and transferred to a sterile centrifuge tube. The concentration of cells in the suspension was determined, and an appropriate dilution was made to obtain a density of 5000 cells/ml. The cells were subcultured into the designated wells of the 96-well bioassay plates (200 microliter cell suspension per well). PBS was added to all the remaining wells to maintain humidity. The plates were then incubated overnight before test article treatment.

Each dose of test article was tested by treating quadruplicate wells of cultures with 100 microliter of each dilution. Those wells designated as solvent controls received an additional 100 microliter of methanol control; negative controls wells received an additional 100 microliters of treatment medium. PBS was added to the remaining wells not treated with test article or medium. The plates were then incubated for approximately 5 days.

At the end of the 5 day incubation, each dose group was examined microscopically to assess toxicity. A 0.5 mg/ml dilution of MTT was made in treatment medium, and the dilution was filtered through a 0.45 micrometer filter to remove undissolved crystals. The medium was decanted from the wells of the bioassay plates. Immediately thereafter, 2000 microliter of the filtered MTT solution was added to all test wells except for the two untreated blank test wells. The two blank wells received 200 microliters of treatment medium. The plates were returned to the incubator for about 3 hours. After incubation, the MET containing medium was decanted. Excess medium was added to each well and the plates were shaken at room temperature for about 2 hours.

The absorbance at 550 nm ($OD_{550}$) of each well was measured with a Molecular Devices (Menlo Park, Calif.) VMax plate reader.

The mean $OD_{550}$ of the solvent control wells and that of each test article dilution, and that of each of the blank wells and the positive control were calculated. The mean $OD_{550}$ of the blank wells was subtracted from the mean of the solvent control wells, and test article wells, respectively to give the corresponding mean $OD_{550}$.

% of Control=corrected mean $OD_{550}$ of Test Article Dilution/corrected mean of $OD_{550}$ of Solvent Control×100

Dose response curves were prepared as semi-log plots with % of control on the ordinate (linear) and the tdst article concentration on the abscissa (logarithmic). The $EC_{50}$ was interpolated from the plots for each test article.

For the test articles administered in methanol, separate responses were prepared to correct for the methanol data.

Adriamycin was used as a positive control. In all cases, it was more toxic than any of the test materials by one or two logs. Adriamycin is one of the more potent agents in current use and one with significant side effects. The peak plasma concentration of other, quite effective chemotherapeutic agents may be 10 to 50 times higher than that of Adriamycin.

The $EC_{50}$ is the concentration at which one half of the cells are killed.

TABLE 2

| Test Material | EC-50 Result (ppm) | | | | | |
|---|---|---|---|---|---|---|
| | HT29 | HT29 | MX1 | MX1 | A549 | A549 |
| Adriamycin | 0.03 | 0.006 | 0.02 | 0.001 | 0.03 | 0.009 |
| benomyl | 0.742 | 0.747 | 1.42 | 2.42 | 0.980 | 1.02 |
| carbendazim | 0.621 | 0.662 | 0.829 | 0.856 | 0.856 | 0.836 |

In normal healthy cells, the following results were obtained. As is evident, the benomyl and carbendazim were much less toxic to normal healthy cells than adriamycin.

TABLE 3

| | Test Material EC-50 | | | | | |
|---|---|---|---|---|---|---|
| | Broncheal Cells | | Keratinocyte Cells | | Fibroblasts | |
| Benomyl | 0.728 | 0.682 | 3.26 | 2.4 | 3.24 | 2.81 |
| Carbendazin | 0.320 | 0.506 | 0.752 | 0.822 | 1.52 | 1.42 |
| Adriamycin | 0.015 | 0.0020 | 0.0035 | 0.0093 | 0.065 | 0.10 |

What is claimed is:

1. A method of preventing cancer or inhibiting metastasis of cancer susceptible to treatment in a subject at risk for developing cancer or metastasis of cancer comprising administering to said subject in need thereof a pharmaceutical composition comprising a therapeutically effective amount of a benzimidazole having the formula:

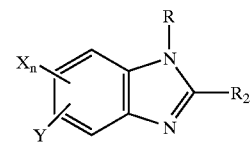

wherein,

X is hydrogen, halogen, alkyl of less than 7 carbon atoms, or alkoxy of less than 7 carbon atoms;

n is a positive integer of less than 4;

Y is hydrogen, chlorine, nitro, methyl, or ethyl;

R is hydrogen or an alkyl group having from 1 to 8 carbon atoms; and $R_2$ is 4-thiazolyl or $NHCOOR_1$ wherein $R_1$ is an aliphatic hydrocarbon of less than 7 carbon atoms.

2. A method according to claim 1 wherein the pharmaceutical composition comprises from about 10 mg to about 6000 mg of said benzimidazole and a safe and effective amount of a pharmaceutically acceptable carrier.

3. A method according to claim 2 wherein said benzimidazole is 2-methoxycarbonylaminobenzilmlidazole.

4. A method according to claim 1 wherein the method is for preventing sarcomas or lymphomas.

5. A method according to claim 1 comprising administering from about 500 mg/kg body weight to about 6000 mg/kg body weight of said benzimidazole, together with a safe and effective amount of a pharmaceutically acceptable carrier.

6. A method according to claim 5 wherein said benzimidazole is administered orally, enterically, intravenously, peritoneally, or by injection.

7. A method according to claim 6 wherein said benzimidazole is administered in a solid form wherein said solid form includes a carrier selected from the group consisting of lactose, sucrose, gelatin and agar.

8. A method according to claim 7 wherein from about 1500 mg/kg to about 5000 mg/kg of said benzimidazole is administered.

9. A method according to claim 6 wherein said benzimidazole is administered in a liquid form, wherein said liquid form is selected from the group consisting of an aqueous solution, an alcohol solution, an emulsion, a suspension, a suspension reconstituted from non-effervescent or effervescent preparations, and a suspension in pharmaceutically acceptable fats or oils.

10. A method according to claim 9 wherein said liquid form further comprises a member selected from the group consisting of suspending agents, diluents, sweeteners, flavorants, colorants, preservatives, emulsifying agents, and coloring agents, and mixtures thereof.

11. A method according to claim 6 wherein said benzimidazole is 2-methoxycarbonylaminobenzimidazole.

12. A method according to claim 1 wherein said cancer is colon cancer.

13. A method according to claim 1 wherein said cancer is pancreatic cancer.

14. A method according to claim 1 wherein said cancer is breast cancer.

15. A method according to claim 1 wherein said cancer is lung cancer.

16. A method according to claim 1 wherein said cancer is leukemia.

17. A method according to claim 1 wherein said cancer is a sarcoma.

18. A method according to claim 1 wherein said benzimidazole is micronized.

19. A method of preventing cancer or inhibiting metastasis of cancer susceptible to treatment in a subject at risk for developing cancer or metastasis of cancer comprising administering to said subject in need thereof a pharmaceutical composition comprising a therapeutically effective amount of a pharmaceutical addition salt of a benzimidazole having the formula:

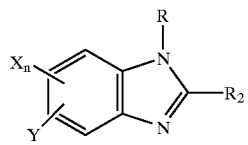

wherein,
X is hydrogen, halogen, alkyl of less than 7 carbon atoms, or alkoxy of less than 7 carbon atoms;
n is a positive integer of less than 4;
Y is hydrogen, chlorine, nitro, methyl, or ethyl;
R is hydrogen or an alkyl group having from 1 to 8 carbon atoms; and
$R_2$ is 4-thiazolyl or $NHCOOR_1$ wherein $R_1$ is an aliphatic hydrocarbon of less than 7 carbon atoms.

20. A method according to claim 19 wherein said pharmaceutical composition comprises a pharmaceutical addition salt of 2-methoxycarbonylaminobenzimidazole.

21. A method according to claim 20 wherein said pharmaceutical addition salt is a chloride salt.

22. A method according to claim 19 wherein said pharmaceutical addition salt is a chloride salt.

23. A method according to claim 19 which comprises administering from about 500 mg/kg body weight to about 6000 mg/kg body weight of said benzimidazole pharmaceutical addition salt.

24. A method according to claim 19 wherein said cancer is selected from the group consisting of colon cancer, pancreatic cancer, breast cancer, lung cancer, leukemia, and a sarcoma.

25. A method according to claim 19 wherein said benzimidazole pharmaceutical addition salt is micronized.

26. A method according to claim 19 wherein said pharmaceutical addition salt is selected from the group consisting of chlorides, bromides, sulfates, nitrates, phosphates, sulfonates, formates, tartrates, maleates, malates, citrates, benzoates, salicylates, ascorbates, and mixtures thereof.

27. A method according to claim 26 wherein said pharmaceutical composition comprises from about 1500 mg to about 5000 mg of said benzimidazole.

28. A method of preventing cancer or inhibiting metastasis of cancer susceptible to treatment in a subject genetically disposed to cancer comprising administering to said subject in need thereof a pharmaceutical composition comprising a therapeutically effective amount of a benzimidazole having the formula:

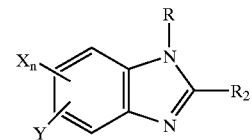

wherein,
X is hydrogen, halogen, alkyl of less than 7 carbon atoms, or alkoxy of less than 7 carbon atoms;
n is a positive integer of less than 4;
Y is hydrogen, chlorine, nitro, methyl, or ethyl;
R is hydrogen or an alkyl group having from 1 to 8 carbon atoms; and
$R_2$ is 4-thiazolyl or $NHCOOR_1$ wherein $R_1$ is an aliphatic hydrocarbon of less than 7 carbon atoms.

* * * * *

UNITED STATES PATENT AND TRADEMARK OFFICE
CERTIFICATE OF CORRECTION

PATENT NO. : 6,423,734 B1
DATED : July 23, 2002
INVENTOR(S) : James B. Camden

It is certified that error appears in the above-identified patent and that said Letters Patent is hereby corrected as shown below:

Column 16,
Line 56, delete "2-methoxycarbonylaminobenzilmlidazole" and replace with
-- 2-methoxycarbonylaminobenzimidazole --.
Line 46, delete "chlorine" and replace with -- chloro --.

Column 17,
Line 51, delete "chlorine" and replace with -- chloro --.

Column 18,
Line 47, delete "chlorine" and replace with -- chloro --.

Signed and Sealed this

Seventeenth Day of December, 2002

JAMES E. ROGAN
*Director of the United States Patent and Trademark Office*